United States Patent [19]

von der Saal et al.

[11] Patent Number: 5,057,526
[45] Date of Patent: Oct. 15, 1991

[54] PHARMACEUTICALLY ACTIVE PYRIDINYL SUBSTITUTED 5,7-DIHYDROPYRROLO-[3,2-F]BENZOXAZOLE-6-ONES

[75] Inventors: Wolfgang von der Saal, Weinheim; Rainer Haag, Mannheim, both of Fed. Rep. of Germany

[73] Assignee: Boehringer Mannheim GmbH, Mannheim, Fed. Rep. of Germany

[21] Appl. No.: 327,827

[22] Filed: Mar. 23, 1989

[30] Foreign Application Priority Data

Mar. 24, 1988 [DE] Fed. Rep. of Germany ....... 3809868

[51] Int. Cl.⁵ .................... A61K 31/44; C07D 498/04
[52] U.S. Cl. .................................. 514/338; 514/361; 514/375; 514/253; 514/314; 514/278; 546/271; 546/15; 546/174; 548/127; 548/218; 544/238
[58] Field of Search .................. 546/271, 15; 514/338, 514/278

[56] References Cited

U.S. PATENT DOCUMENTS 4,695,567 9/1987 Mertens et al. .................... 514/254
4,730,003 3/1988 Von der Saal et al. ............ 546/271

FOREIGN PATENT DOCUMENTS 0189103 7/1986 European Pat. Off. .
0214592 3/1987 European Pat. Off. .

OTHER PUBLICATIONS

K. H. Fye, "Rheumatic Diseases", ch. 26 of D. P. Stites et al., *Basic and Clinical Immunology*, pp. 430–459 (4th ed. 1982) (Fye).
I. M. Roitt et al., *Immunology*, pp. 8.3 and 23.11 (1989) ("Roitt").
N. F. Rothfield, "The Relation of Immunoglobulin Class, Pattern of Antinuclear Antibody, and Complement-Fixing Antibodies to DNA in Sera from Patients with Systemic Lupus Erythematosus", *J. Clin. Invest.* 46, 1785–94 (1967) (Rothfield).
M. Reichlin et al., "Antigens and Antibodies Characteristic of Systemic Lupus Erythematosus", *Bull. Rheum. Dis.* 24, 756–60 (1974) (Reichlin).
J. L. Abruzzo et al., "IgG and Anti-IgG Antibodies in Rheumatoid Arthritis and Certain Other Conditions", *Ann. Rheum. Dis.* 33, 258–61 (1974) (Abruzzo).
Bichner, Uwe, Nature 324:307 (1986).
Klatzman et al., Nature, 319:10–11 (1986).
Klatzman et al., Immunology Today, 7:291–296 (1986).
Van Der Lilie Brit J. Hemat., 67:109–114 (1987).
Saxon, Andrew et al., J. Allergy Clin. Immunol., 81:796–802 (1988).

*Primary Examiner*—Jane T. Fan
*Attorney, Agent, or Firm*—Felfe & Lynch

[57] ABSTRACT

Compounds of the formula I

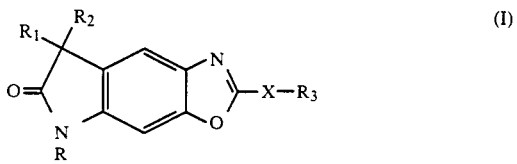

wherein R is a hydrogen atom or an alkyl radical, $R_1$ is a hydrogen atom or an alkyl, alkenyl or a cycloalkyl radical, $R_2$ is a hydrogen atom or an alkyl, alkenyl, alkylcarbonyl, alkoxycarbonyl, aminocarbonyl or hydrazinocarbonyl radical or $R_1$ and $R_2$, together with the carbon atom to which they are attached, form a cycloalkyl ring, X is a valency bond or an alkylene or vinylene radical, $R_3$ is an aromatic heterocyclic five-membered ring containing 1 to 4 heteroatoms or pyridinyl which the five- and six-membered rings are optionaly substituted one or more times by alkyl, alkoxy, alkoxycarbonyl, carboxyl, alkylthio, hydroxyl, nitro, amino, halogen or cyano and the tautomers, optically-active forms and physiologically acceptable salts thereof with inorganic and organic acids.

These compounds are useful for treatment of immunological disorders or autoimmune diseases such as aids-/ARC, rheumatoid arthritis, lupus erythematosus and to suppress rejection reactions after organ/tissue transplants.

17 Claims, No Drawings

PHARMACEUTICALLY ACTIVE PYRIDINYL SUBSTITUTED 5,7-DIHYDROPYRROLO-[3,2-F]BENZOXAZOLE-6-ONES

The present invention is concerned with new heterocyclic substituted 5,7-dihydropyrrolo[3,2-f]benzoxazol-6-ones, processes for the preparation thereof and pharmaceutical compositions containing them.

The new compounds according to the present invention have the general formula:

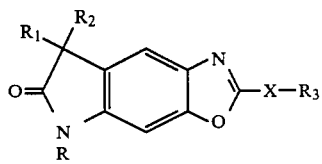

wherein R is a hydrogen atom or an alkyl radical, $R_1$ is a hydrogen atom or an alkyl, alkenyl or cycloalkyl radical, $R_2$ is a hydrogen atom or an alkyl, alkenyl, alkylcarbonyl, alkoxycarbonyl, aminocarbonyl or hydrazinocarbonyl radical or $R_1$ and $R_2$, together with the carbon atom to which they are attached, form a cycloalkyl ring, X is a valency bond or an alkylene or vinylene radical and $R_3$ is an aromatic heterocyclic five-membered ring containing 1 to 4 heteroatoms or an aromatic heterocyclic six-membered ring containing 1 to 5 heteroatoms, in which the heteroatoms are the same or different and are oxygen, sulphur or nitrogen atoms and, if desired, one or more nitrogen atoms can carry an oxygen atom and the five- and six-membered rings are optionally substituted one or more times by alkyl, alkoxy, alkoxycarbonyl, carboxyl, alkylthio, hydroxyl, nitro, amino, halogen or cyano and, if desired, can be condensed with a phenyl ring or an aromatic five- or six-membered ring containing 1 to 4 heteroatoms to form a bicyclic radical; and the tautomers, optically-active forms and physiologically acceptable salts thereof with inorganic and organic acids.

When the compounds of general formula (I) contain an asymmetric atom, the optically-active compounds and the racemic mixtures are also the subject of the present invention. Optically active compounds can be obtained from the racemic mixtures, in known manner, via diastereomeric salts. For splitting off the racemic mixtures, optically active acid or bases, such as tartaric acid, malic acid or camphor sulfonic acid can be used.

The new compounds of general formula (I) possess valuable pharmacological properties. In particular, they can be used as immunosuppressives in the case of immune diseases, for example rheumatoid arthritis, diabetes mellitus type I, psoriasis, lupus systemicus erythematosus and the like, as well as for the therapy of rejection reactions after organ/tissue transplantations, for example of skin, bone marrow, kidneys and the like. Furthermore, they can be used therapeutically in the case of all those diseases in which a polyclonal B cell activation/proliferation could be of pathophysiological, symptomatic and/or clinical relevance, i.e. besides autoimmune diseases, also in the case of ARC/AIDS, as well as in the case of viral infections of any genesis. Furthermore, the above-mentioned compounds act cytostatically/cytotoxically and are, therefore, especially suitable for the treatment of B cell/T cell/plasma cell leukaemias or neoplasias, for example chronic lymphatic leukaemia, lymphoblastic lymphoma, multiple myeloma and the like.

In general formula (I), the substituents $R_1$ and $R_2$ can be the same or different and are hydrogen atoms, straight-chained or branched, saturated or unsaturated alkyl radicals containing 1 to 6 or 2 to 6 carbon atoms, respectively, or carbonyl groups substituted by alkyl, alkoxy, amino or hydrazino, each alkyl radical being straight-chained or branched and containing 1 to 6 or 2 to 6 carbon atoms, respectively.

Especially, however, $R_1$ and $R_2$ are hydrogen atoms or methyl, ethyl, allyl, acetyl, propionyl, methoxycarbonyl, ethoxycarbonyl or hydrazinocarbonyl radicals.

If only $R_2$ is a hydrogen atom, then $R_1$ is preferably a straight-chained alkyl radical containing up to 6 carbon atoms or a branched alkyl radical or a cycloalkyl radical containing 3 to 7 carbon atoms or a carbonyl group substituted by alkyl, alkoxy, amino or hydrazino. Preferred in this sense are the methyl, ethyl, isopropyl, isobutyl, pentyl, cyclopentyl, cyclohexyl, allyl, acetyl, propionyl, methoxycarbonyl, ethoxycarbonyl and hydrazinocarbonyl radicals.

$R_1$ and $R_2$, together with the carbon atom to which they are attached, can also form a cycloalkyl ring containing 3 to 8 carbon atoms and preferably a spirocyclopropyl, spirocyclobutyl, spirocyclopentyl and spirocyclohexyl radical.

R is preferably a hydrogen atom but can also be an alkyl radical containing up to 6 carbon atoms, for example a methyl, ethyl or isopropyl radical.

If, in general formula (I), X is an alkylene radical, then this is to be understood to include a chain containing up to 6 carbon atoms, which can also be branched. Especially preferably, X is a methylene, ethylene, propylene or butylene radical.

The heterocyclic five-membered rings containing 1 to 4 heteroatoms and the heterocyclic six-membered rings containing 1 to 5 heteroatoms, the heteroatoms of the above-mentioned five- or six-membered rings being the same or different and being nitrogen, oxygen or sulphur atoms and optionally carrying an oxygen atom on one or more nitrogen atoms, given in the case of $R_3$ are preferably pyrrole, furan, thiophene, pyrazole, imidazole, thiazole, isothiazole, oxazole, isoxazole, triazole, thiadiazole, oxadiazole, pyrazine, N,N'-dioxypyrazine, pyrimidine, N,N'-dioxypyrimidine, pyridazine, oxazine, thiazine, triazine, tetrazine, pyridine or N-oxypyridine radicals.

Alkyl, alkoxy and alkylthio substituents in the heterocyclic five- and six-membered rings can contain up to 6 and preferably up to 5 carbon atoms, methyl, ethyl, methoxy, ethoxy, methylthio and ethylthio radicals being preferred.

Halogen is to be understood to be a fluorine, chlorine or bromine atom and preferably a chlorine atom.

If the aromatic heterocyclic five- and six-membered rings are condensed with a phenyl ring, then the indole, indazole, benzimidazole, quinoline, isoquinoline, cinnoline, phthalazine, quinazoline, quinoxaline, benzofuran, benzothiophene, benzoxazole, benzisoxazole, benzothiazole, benzoisothiazole, benzotriazole and benzothiadiazole radicals are preferred.

If the aromatic heterocyclic five- and six-membered rings are condensed with a further aromatic heterocyclic five- or six-membered ring to give a bicyclic radical, then the naphthyridine, pteridine, purine, indolizine, thiophene[2,3-b]pyrazine and imidazol[1.2-a]pyridine radicals are preferred.

Especially preferred compounds of general formula (I) are those in which R is a hydrogen atom, $R_1$ and $R_2$ are the same and are methyl radicals or $R_1$ and $R_2$, together with the carbon atom to which they are attached, form a spirocyclopentyl ring, X is a valency bond, a $C_1$-$C_4$-alkylene radical or a vinylene radical and W. Cornforth in Heterocyclic Compounds (R. C. Elderfield, editor), Vol. 5, pub. J. Wiley & Sons, New York 1957, p. 418 et seq. This involves the following basic processes: (1 a) and (2 c) nitration; (1 b) and (2 b) esterification; (2 a) and (3 c) reduction; (3 a) formation of a Schiff's base by reaction with an aldehyde; (3 b) ring closure by heating with a carboxylic acid derivative; (4) ring closure by oxidation.

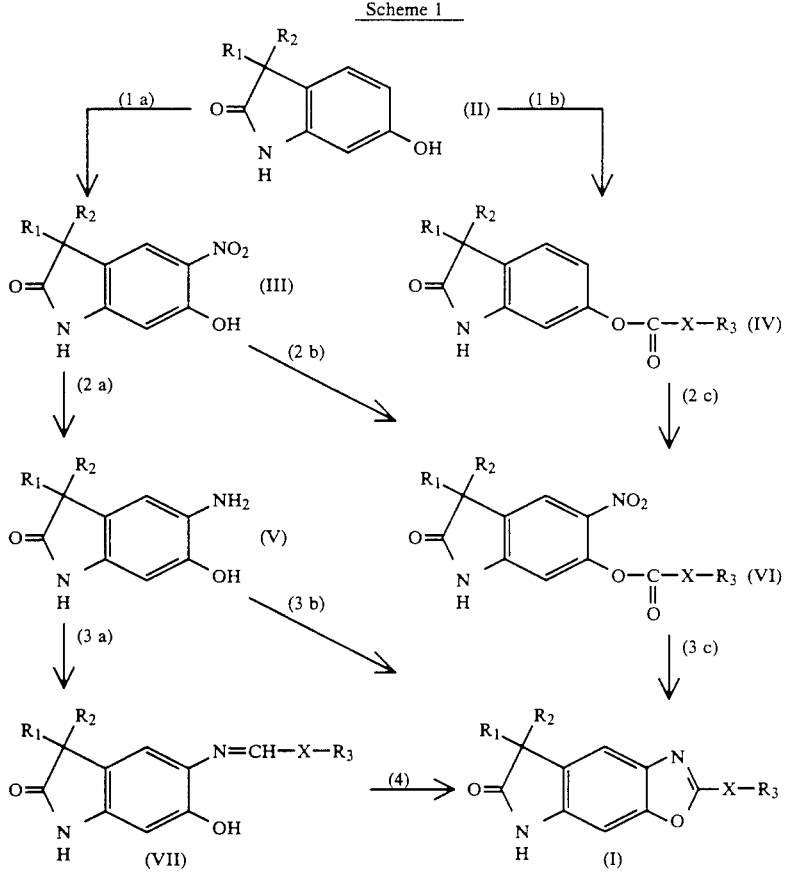

Scheme 1

$R_3$ is a pyrrolyl, furyl, thienyl, pyrazolyl, imidazolyl, isothiazolyl, thiazolyl, oxazolyl, triazolyl, tetrazolyl, thiadiazolyl, isoxazolyl, oxadiazolyl, pyridinyl, N-oxypyridinyl, pyrazinyl, N,N'-dioxypyrazinyl, pyrimidinyl, N,N'-dioxypyrimidinyl, pyridazinyl, oxazinyl, thiazinyl, triazinyl or tetrazinyl radical, as well as their $C_1$-$C_4$-alkyl, for example methyl- or ethyl-, $C_1$-$C_4$-alkoxy-, for example methoxy- or ethoxy-, $C_1$-$C_4$-alkylthio-, for example methylthio- or ethylthio- and halogen-, for example chlorine-, substituted derivatives, or is an indolyl, indazolyl, quinolinyl, isoquinolinyl or imidazo[1,2-a]pyridinyl radical.

The compounds of general formula (I) and the tautomers thereof can be prepared by known processes. Especially advantageous are the processes shown hereinafter in schemes 1-3.

The process illustrated in scheme 1 starts from 1,3-dihydro-6-hydroxy-2H-indol-2-ones of general formula (II), in which $R_1$ and $R_2$ have the above-given meanings. These compounds are known or can be prepared analogously to the procedures described in International Patent Application WO 83/02610 and by Th. Wieland and O. Unger, Chem. Ber., 96, 253/1963.

The further steps 1-4 of scheme 1 follow known methods of benzoxazole syntheses as are described by J.

Step 1 a

By the nitration of compounds of general formula (II), compounds are obtained of general formula (III), in which $R_1$ and $R_2$ have the above-given meanings. The nitration is preferably carried out with nitric acid in sulphuric acid at a temperature of from $-20°$ C. to $+50°$ C. It can, however, also be carried out without sulphuric acid or in place thereof in water, glacial acetic acid or acetic anhydride or with nitrogen pentoxide in carbon tetrachloride in the presence of phosphorus pentoxide. As nitrating agents, there can also be used anhydrides, for example acetyl nitrate, or nitryl halides with ferric chloride, methyl nitrate and boron trifluoride or nitronium salts, such as $NO_2BF_4$, $NO_2PF_6$ or $NO_2CF_3SO_3$. For the nitration, there can also be used a mixture of nitric acid and nitrous acid, which provides dinitrogen tetroxide as the actual nitrating species.

Step 1 b

Compounds of general formula (IV), in which $R_1$, $R_2$, $R_3$ and X have the above-given meaning, are prepared from compounds of general formula (II) by reaction with the carboxylic acids or derivatives derived therefrom of the general formula:

$$Y-X-R_3 \quad (VIII)$$

in which $R_3$ and X have the above-given meanings and Y is a carboxyl group or an alkoxycarbonyl, alkoxycarbonyloxycarbonyl or halocarbonyl radical. If Y is a carboxyl group, then the reaction between the phenol of general formula (II) and the carboxylic acid of general formula (VIII) takes place in an inert solvent, for example dichloromethane, toluene, xylene or dimethylformamide, at a temperature of from 50° to 150° C. and preferably at the boiling point of the solvent. The water formed is removed either by azeotropic distillation or by means of a condensation agent, for example phosphorus oxychloride, thionyl chloride, sulphuric acid, phosphoric acid or molecular sieve. Other reagents which accelerate the reaction include dicyclohexylcarbodiimide, N,N'-carbonyldiimidazole, boron trifluoride, trifluoroacetic anhydride, boric acid/sulphuric acid and polymer-bound aluminium chloride.

Step 2 a

Compounds of general formula (III) are converted into compounds of general formula (V) by reduction of the nitro group.

The reduction is preferably carried out in a solvent or solvent mixture, for example water, methanol, ethanol, glacial acetic acid, ethyl acetate or dimethylformamide, with hydrogen in the presence of a catalyst, for example Raney nickel, platinum or palladium/charcoal, with a metal, such as iron, tin or zinc, in the presence of an acid, with salts, such as ferrous sulphate, stannous chloride, sodium sulphide, sodium hydrogen sulphite or sodium dithionite, with hydrazine in the presence of Raney nickel at a temperature of from 0° to 100° C. but preferably at ambient temperature. An isolation of compounds of general formula (V) can, however, also be omitted, the solutions then being further reacted as described hereinafter in step 3 a.

Step 2 b

The compounds of general formula (III) can be converted by esterification into compounds of general formula (VI). The esterifications are carried out as described in step 1 b.

Step 2 c

The compounds of general formula (IV) can be converted by nitration into compounds of general formula (VI), the nitration being carried out as described in step 1 a.

Step 3 a

The compounds of general formula (V) are converted into compounds of general formula (VII) by reacting them with aldehydes of the general formula:

$$OHC-X-R_3 \quad (IX)$$

in which $R_3$ and X have the above-given meanings. For this purpose, the compounds are mixed together in an inert solvent, for example dichloromethane, toluene, xylene, chlorobenzene or diethyl ether, and isolated by stripping off of the solvent. However, a preferred method is not to isolate the compounds of general formula (VII) but rather immediately to react them further to give compounds of general formula (I) (see step 4).

Step 3 b

The compounds of general formula (V) can be cyclised to give compounds of general formula (I) by reacting them with carboxylic acids or their derivatives of the general formula:

$$Z-X-R_3 \quad (X)$$

in which X and $R_3$ have the above-given meanings and Z can be a carboxyl group or an alkoxycarbonyl, alkoxycarbonyloxycarbonyl, chlorocarbonyl, aminocarbonyl or nitrile group. The reactions can be carried out without the use of a solvent, i.e. in the melt, at a temperature of from 150° to 250° C.

If the compound of general formula (X) is a carboxylic acid, then the reaction with a compound of general formula (V) takes place in the presence of a water-removing agent, preferably in polyphosphoric acid, at a temperature of from 50° to 250° C. and preferably of from 100° to 200° C.

If the compound of general formula (X) is a carboxylic acid derivative, then the reaction with a compound of general formula (V) takes place in an inert solvent and preferably in methylene chloride or pyridine. For completion of the cyclisation, heating is subsequently carried out in a solvent or solvent mixture, for example ethanol, isopropanol, glacial acetic acid, benzene, chlorobenzene, glycol, diethylene glycol dimethyl ether, sulpholan or dimethylformamide, to a temperature of from 50° to 250° C. but preferably to the boiling temperature of the solvent or solvent mixture, optionally in the presence of a condensation agent, for example phosphorus oxychloride, thionyl chloride, p-toluenesulphonic acid, hydrochloric acid, sulphuric acid, phosphoric acid or polyphosphoric acid, or optionally also in the presence of a base, for example sodium hydroxide, potassium methylate or potassium tert.-butylate.

Step 3 c

The reduction of compounds of general formula (VI) leads directly to the ring closure, the compounds of general formula (I) being isolated. The reduction is carried out as described in step 2 a.

Step 4

From the Schiff bases of general formula (VII), the compounds of general formula (I) are obtained by oxidation. The reaction is preferably carried out in an alcoholic medium with heating to reflux in the presence of atmospheric oxygen and a catalytic amount of an acid, for example p-toluenesulphonic acid, or in the presence of atmospheric oxygen and of a catalyst, for example pyrolusite, in acidic medium, for example in glacial acetic acid, at ambient temperature, or with lead tetraacetate, chloranil, N-bromosuccinimide, N-iodosuccinimide, sulphuryl chloride, hydrogen peroxide or iron hexacyanoferrate.

An especially preferred process for the preparation of compounds of general formula (I) from compounds of general formula (II) comprises the nitration (step 1 a) and subsequent reduction (step 2 a). The compounds of general formula (V) are now not isolated but rather reacted directly with the aldehydes of general formula (IX) (step 3 a) in the presence of an oxidation agent (step 4) or with the carboxylic acid derivatives of general formula (X) (step 3 b).

A further preferred process, starting from the 5-methyl-6-nitrobenzoxazoles of general formula (XI), in which $R_3$ and X have the above-given meanings, is illustrated in scheme 2.

Compounds of general formula (XI) are known (see R. D. Haugwitz et al., J. Med. Chem., 25, 969–974/1982) or can be prepared by procedures mentioned in this literature reference. The synthesis route illustrated in scheme 2 follows a known process (Reissert synthesis) for the preparation of 1,3-dihydro-2H- indol-2-ones, such as is described, for example, in the International Patent Application WO 83/02610 (R. Anchi, Sandoz AG, Basel, 19.1.83). It involves the following basic processes: (5) reaction with oxalic acid diethyl ester in the presence of a base; (6 a) alkylation or acylation; (6 b) and (7 a) alkaline hydrolysis; (8 a) and (7 b) reaction with hydrogen peroxide; (9 a) and (8 b) catalytic hydrogenation and heating; (9 b) alkylation or acylation.

ether, toluene or xylene, in the presence of a base, for example potassium or sodium methylate or ethylate or potassium tert.-butylate, at a temperature of from −20° C. to 50° C. and preferably at ambient temperature. The compounds of general formula (XII) precipitate out after some time in the form of the sodium or potassium salts or are obtained by evaporation of the solvent.

Step 6 a

By alkylation, from compounds of general formula

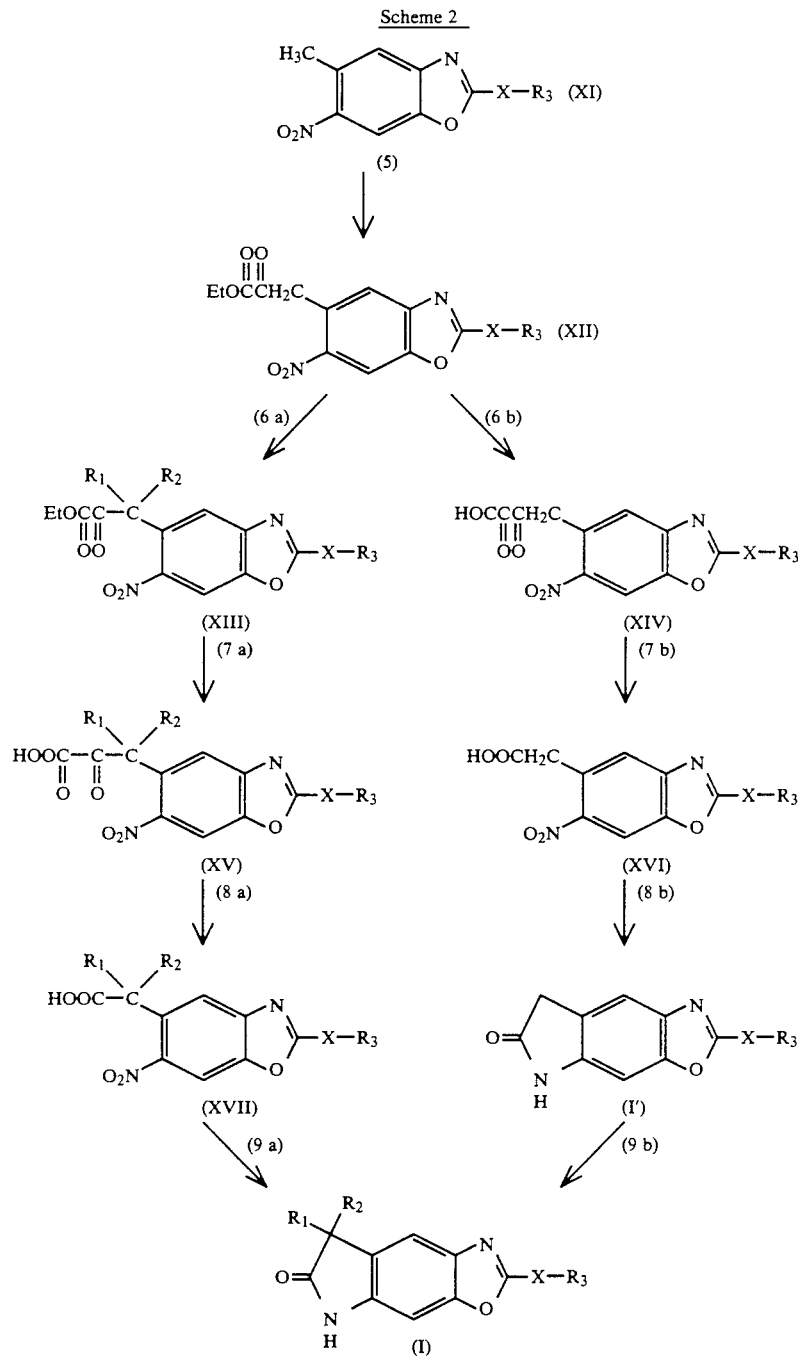

Step 5

By the reaction of compounds of general formula (XI) with oxalic acid diethyl ester, there are obtained compounds of general formula (XII), in which $R_3$ and X have the above-given meanings. This reaction is carried out in an inert solvent, such as dichloromethane, diethyl (XII) are obtained compounds of general formula (XIII). This alkylation is carried out in an inert solvent, for example dichloromethane, diethyl ether, toluene or xylene, in the presence of a base, for example aqueous sodium hydroxide solution or aqueous potassium hydroxide solution, if desired in the presence of a phase transfer catalyst, with an alkylation agent which transfers the radicals $R_1$ and $R_2$. As alkylation agents, there can be used, for example, alkyl halides or alkyl sulphates.

Step 6 b

The compounds of general formula (XII) are saponified under alkaline conditions to give compounds of general formula (XIV), in which X and $R_3$ have the above-given meanings. This saponification is best carried out in water or in an alcohol or in a mixture of them both in the presence of a base, for example aqueous sodium hydroxide solution or aqueous potassium hydroxide solution, at a temperature of from 0° to 100° C. and preferably at ambient temperature.

Step 7 a

By alkaline saponification as described in step 6 b, there are obtained compounds of general formula (XV), in which X and $R_3$ have the above-given meanings. This step can also be avoided when oxidising compounds of general formula (XIII) directly as described hereinafter in step 8 a.

Step 7 b

Compounds of general formula (XII) or (XIV) are oxidised to compounds of general formula (XVI), in which X and $R_3$ have the above-given meanings.

The compounds of general formula (XII) or (XIV) are preferably dissolved in water or an alcohol and oxidised in the presence of a base, for example aqueous sodium hydroxide solution or aqueous potassium hydroxide solution, with hydrogen peroxide at a temperature of from −20° C. to +50° C. and preferably at ambient temperature. After acidification, in general the compounds of general formula (XVI) precipitate out of the solution or they are obtained by evaporation of the solution.

Step 8 a

Compounds of general formula (XVII) are obtained by the oxidation of compounds of general formula (XIII) or (XV), the process being carried out as described for step 7 b.

Step 8 b

Compounds of general formula (I'), in which X and $R_3$ have the above-given meanings, are obtained from compounds of general formula (XVI) by reduction of the nitro group and subsequent heating. The compounds of general formula (I') differ from those of general formula (I) in that $R_1$ and $R_3$ are both hydrogen atoms. The reduction of the nitro group is carried out as described in step 2 a, cyclisation to give compounds of general formula (I') thereby partly taking place directly.

Cyclisation can, if desired, be completed by heating, after the reduction, preferably in a solvent, for example ethanol, isopropanol, glacial acetic acid, benzene, toluene, chlorobenzene, glycol, ethylene glycol dimethyl ether, sulpholan or dimethylformamide or mixtures of these solvents, to a temperature of from 50° to 220° C. but preferably to the boiling temperature of the reaction mixture, optionally in the presence of a condensation agent, for example phosphorus oxychloride, thionyl chloride, p-toluenesulphonic acid, hydrochloric acid, sulphuric acid, phosphoric acid or polyphosphoric acid, or optionally also in the presence of a base, for example sodium hydroxide, sodium ethylate or potassium tert.-butylate. However, cyclisation can also be carried out without the use of solvents and/or condensation agents.

Step 9 a

The compounds of general formula (XVII) are reduced and cyclised to compounds of general formula (I) as is described for step 8 b.

Step 9 b

Compounds of general formula (I), in which $R_3$ and X have the above-given meanings and in which $R_1$ and $R_2$ are hydrogen atoms (=general formula I'), can be converted into compounds of general formula (I), in which $R_1$, $R_2$, $R_3$ and X have the above-given meanings. For this purpose, it is necessary to replace the free NH proton by a protective group and preferably by the acetyl radical. Subsequently, the alkylation or acylation is carried out as described in step 6 a and the acetyl protective radical is split off.

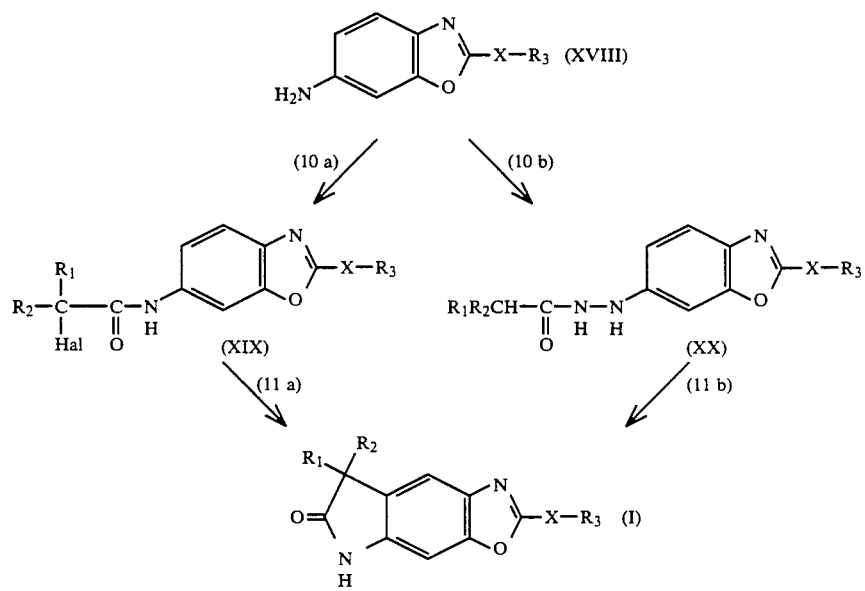

A third preferred process starts, as scheme 3 shows, from 6-aminobenzoxazoles of general formula (XVIII), in which X and $R_3$ have the above-given meanings. The compounds of general formula (XVIII) are known from the literature (R. Haugewitz et al., J. Med. Chem., 25, 969 et seq./1982) or can be prepared according to the processes described therein.

In the case of the process in scheme 3, the following basic processes are used: (10 a) and (11 a) follow the oxindole synthesis according to Stolle as described by P. L. Julian, E. W. Meyer and H. C. Printy (R. C. Elderfield, editor), Heterocyclic Compounds, Vol. 3, pub. Wiley and Sons, New York, 1952, p. 142 et seq. and (10 b) and (11 b) follow the oxindole synthesis according to Brunner, as described in ibid., p. 141 et seq.

Step 10 a

Compounds of general formula (XVIII) are acylated by α-halocarboxylic acid derivatives and preferably by α-halo acid chlorides or bromides of the general formula:

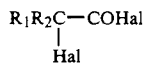

$$R_1R_2C-COHal \atop Hal \qquad (XXI)$$

in which $R_1$ and $R_2$ have the above-given meanings and Hal is a halogen atom. In general, working is carried out at a temperature of from $-10°$ C. to ambient temperature. It is preferable to proceed in such a manner that, according to the Schotten-Baumann reaction, to the aqueous solution of the amine, which also contains a base, for example an alkali metal hydroxide, sodium carbonate or pyridine, there is slowly added dropwise the acid chloride with ice cooling and the reaction mixture is subsequently left to stand for some time at ambient temperature. The reaction can be carried out not only in water but also in an organic solvent, for example methylene chloride, diethyl ether, benzene or toluene. Also without acid-binding agents, the amines can be acylated almost quantitatively by carboxylic acid chlorides by boiling the amine and the carboxylic acid chloride in an inert solvent, for example methylene chloride, benzene or toluene, up to the ending of the gas evolution, which takes 1 to 24 hours. However, if an acid-binding agent, for example triethylamine or pyridine, is added thereto in small excess, then the reaction proceeds to completion even at a temperature of from $-10°$ C. to ambient temperature.

Step 10 b

From the compounds of general formula (XVIII), there are obtained the compounds of general formula (XX), in which $R_1$, $R_2$, $R_3$ and X have the above-given meanings, in a three-step one-pot process by diazotising the compounds of general formula (XVIII), reducing the diazonium group to the hydrazine and reacting this with an acid chloride of the general formula:

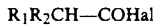

$$R_1R_2CH-COHal \qquad (XXII),$$

in which $R_1$ and $R_2$ have the above-given meanings and Hal is a halogen atom.

The diazotisation of the amines (XVIII) is preferably carried out under neutral or acidic conditions in a polar solvent, for example water, methanol, ethanol, glacial acetic acid, hydrochloric acid, sulphuric acid or phosphoric acid, at a temperature of from $-70°$ C. to $+50°$ C. and preferably of from $-5°$ C. to $+10°$ C.

For the diazotisation, there are preferably used inorganic salts or organic esters of nitrous acid, for example sodium or potassium nitrite or amyl nitrite.

The reduction of the diazonium salts is usually carried out in one of the above-mentioned solvents in which the diazotisation was carried out at a temperature of from $-50°$ C. to the boiling point of the solvent but preferably of from $0°$ C. to $80°$ C. using, as reducing agent, an alkali metal sulphite, sulphur dioxide, a dithionite, stannous chloride, zinc dust, iron, sodium amalgam, triphenyl phosphine or an endiol or also an electrochemical reduction.

The hydrazines are now acylated according to the process described in step 10 a.

Step 11 a

For the ring closure, compounds of general formula (XIX) are finely ground with aluminium chloride and heated to a temperature of from 100° to 270° C. or the reaction is carried out in a solvent, for example carbon disulphide or nitrobenzene. Instead of aluminium chloride, there can also be used zinc chloride or some other strong acid. Cyclisation is also possible photochemically analogously to the description in Heterocycles, 8, 2551/1977.

Step 11 b

The ring closure of hydrazides of general formula (XX) is carried out in a basic medium at an elevated temperature. For this purpose, the hydrazides (XX) are intimately mixed with lime, calcium carbonate or sodium hydride and heated to a temperature of from 150° to 250° C. The reaction can also be carried out in a high boiling solvent, for example diphenyl ether.

The compounds of general formula (I) obtained according to one of the above-described processes and the tautomers thereof can subsequently, if desired, be converted into other compounds of general formula (I) and/or converted into physiologically acceptable salts of an organic and inorganic acid.

The conversion of compounds of general formula (I) into other compounds of general formula (I) applies, for example, to the following:

a) For the hydrogenation of a vinylene compound ($X=-CH=CH-$) into a corresponding ethylene compound ($X=-CH_2-CH_2-$). The hydrogenation is preferably carried out in a solvent, for example water, water/ethanol, methanol, glacial acetic acid, ethyl acetate or dimethylformamide, with hydrogen in the presence of a hydrogenation catalyst, for example Raney nickel, platinum or palladium/charcoal.

b) For the oxidation of a five- or six-membered ring containing one or more nitrogen atoms to give the corresponding N-oxide. The oxidation is advantageously carried out with one or more equivalents of the oxidation agent used, for example with hydrogen peroxide in glacial acetic acid, trifluoroacetic acid or formic acid at 20° to 100° C. or in acetone at 0° to 60° C., with a per acid, for example performic acid or m-chloroperbenzoic acid, in glacial acetic acid, trifluoroacetic acid, methylene chloride or chloroform at a temperature of from 0° to 60° C.

c) For the conversion of a compound of general formula (I), in which $R_2$ is an alkoxycarbonyl radical, into a compound of general formula (I), in which $R_2$ is a hydrazinocarbonyl radical.

Furthermore, the so obtained compounds of general formula (I) can subsequently, if desired, be converted into physiologically acceptable acid-addition salts with inorganic and organic acids. As acids herefor, there can be used, for example, hydrochloric acid, hydrobromic acid, sulphuric acid, phosphoric acid, fumaric acid, succinic acid, tartaric acid, citric acid, lactic acid, maleic acid or methanesulphonic acid.

For the production of pharmaceutical compositions, the compounds of general formula (I) are mixed in known manner with appropriate pharmaceutical carrier substances, aroma, flavouring and colouring materials and formed, for example, into tablets or dragees or, with the addition of appropriate adjuvant materials, suspended or dissolved in water or an oil, for example olive oil.

The new compounds according to the present invention of general formula (I) and the salts thereof can be administered enterally or parenterally in liquid or solid form. As injection medium, there is preferably used water which contains the additives usual in the case of injection solutions, for example stabilising agents, solubilising agents and/or buffers.

Examples of such additives include tartrate and citrate buffers, ethanol, complex formers (such as ethylenediamine-tetraacetic acid and the non-toxic salts thereof) and high molecular weight polymers (such as liquid polyethylene oxide) for viscosity regulation. Examples of solid carrier materials include starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The compounds according to the present invention are usually administered in amounts of from 10 to 2000 mg. per day, referred to 75 kg. body weight. It is preferred to administer 2 or 3 times per day 1 or 2 tablets with an active material content of 10 to 1500 mg. The tablets can also be retarded, in which case, 1 or 2 tablets containing 1 to 500 mg. of active material are administered once per day. The active material can also be given by injection 1 to 8 times per day or by continuous infusion, in which case amounts of 10 to 1000 mg. per day normally suffice.

Preferred in the meaning of the present invention are, apart from the compounds mentioned in the Examples, the following:

2-(N-oxy-3-pyridinyl)-7,7-dimethyl-5,7-dihydropyrrolo[3,2-f]benzoxazol-6-one
2-(N-oxy-2-pyridinyl)-7,7-dimethyl-5,7-dihydropyrrolo[3,2-f]benzoxazol-6-one
2-(2-chloro-4-pyridinyl)-7,7-dimethyl-5,7-dihydropyrrolo[3,2-f]benzoxazol-6-one
2-(2-hydroxy-4-pyridinyl)-7,7-dimethyl-5,7-dihydropyrrolo[3,2-f]benzoxazol-6-one
2-(3-hydroxy-4-pyridinyl)-7,7-dimethyl-5,7-dihydropyrrolo[3,2-f]benzoxazol-6-one
2-(2,6-dihydroxy-4-pyridinyl)-7,7-dimethyl-5,7-dihydropyrrolo[3,2-f]benzoxazol-6-one
2-(6-methyl-3-pyridinyl)-7,7-dimethyl-5,7-dihydropyrrolo[3,2-f]benzoxazol-6-one
2-(2-methyl-5-pyrimidinyl)-7,7-dimethyl-5,7-dihydropyrrolo[3,2-f]benzoxazol-6-one
2-(5-pyrimidinyl)-7,7-dimethyl-5,7-dihydropyrrolo[3,2-f]benzoxazol-6-one
2-(2-hydroxy-5-pyrimidinyl)-7,7-dimethyl-5,7-dihydropyrrolo[3,2-f]benzoxazol-6-one
2-(3-quinolinyl)-7,7-dimethyl-5,7-dihydropyrrolo[3,2-f]benzoxazol-6-one
2-(6-hydroxy-3-pyridazinyl)-7,7-dimethyl-5,7-dihydropyrrolo[3,2-f]benzoxazol-6-one
2-(2-indolyl)-7,7-dimethyl-5,7-dihydropyrrolo[3,2-f]benzoxazol-6-one
2-(3-indolyl)-7,7-dimethyl-5,7-dihydropyrrolo[3,2-f]benzoxazol-6-one
2-(5-methyl-3-pyrazolyl)-7,7-dimethyl-5,7-dihydropyrrolo[3,2-f]benzoxazol-6-one
2-(1,2,4-triazol-3-yl)-7,7-dimethyl-5,7-dihydropyrrolo[3,2-f]benzoaxazol-6-one
2-(1,2,3-thiadiazol-5-yl)-7,7-dimethyl-5,7-dihydropyrrolo[3,2-f]benzoxazol-6-one
2-(2-pyrrolyl)-7,7-dimethyl-5,7-dihydropyrrolo[3,2-f]benzoxazol-6-one
2-(4-thiazolyl)-7,7-dimethyl-5,7-dihydropyrrolo[3,2-f]benzoxazol-6-one
2-(4-imidazolyl)-7,7-dimethyl-5,7-dihydropyrrolo[3,2-f]benzoxazol-6-one
2-(1,2,5-thiadiazol-3-yl)-7,7-dimethyl-5,7-dihydropyrrolo[3,2-f]benzoxazol-6-one
2-(5-methylthio-1,3,4-oxadiazol-2-yl)-7,7-dimethyl-5,7-dihydropyrrolo[3,2-f]benzoxazol-6-one
2-(5-methoxycarbonyl-1,2,3-triazol-4-yl)-7,7-dimethyl-5,7-dihydropyrrolo[3,2-f]benzoxazol-6-one
2-(5-carboxy-1,2,3-triazol-4-yl)-7,7-dimethyl-5,7-dihydropyrrolo[3,2-f]benzoxazol-6-one
2-(2-thenyl)-7,7-dimethyl-5,7-dihydropyrrolo[3,2-f]benzoxazol-6-one
2-(1-methyl-1,2,3-triazol-4-yl)-7,7-dimethyl-5,7-dihydropyrrolo[3,2-f]benzoxazol-6-one
2-(4-butyl-2-pyridinyl)-7,7-dimethyl-5,7-dihydropyrrolo[3,2-f]benzoxazol-6-one
2-(2-benzofuranyl)-7,7-dimethyl-5,7-dihydropyrrolo[3,2-f]benzoxazol-6-one
2-(2-indolisinyl)-7,7-dimethyl-5,7-dihydropyrrolo[3,2-f]benzoxazol-6-one
2-[2-(benzimidazolyl)-ethenyl]-7,7-dimethyl-5,7-dihydropyrrolo[3,2-f]benzoxazol-6-one
2-(5-benzothiadiazolyl)-7,7-dimethyl-5,7-dihydropyrrolo[3,2-f]benzoxazol-6-one
2-(2-thiopheno[2,3-f]pyrazinyl)-7,7-dimethyl-5,7-dihydropyrrolo[3,2-f]benzoxazol-6-one
2-(2-methyl-5-thiazolyl)-7,7-dimethyl-5,7-dihydropyrrolo[3,2-f]benzoxazol-6-one
2-(3-thienyl)-7,7-dimethyl-5,7-dihydropyrrolo[3,2-f]benzoxazol-6-one
2-(4-pyridinyl)-7,7-diethyl-5,7-dihydropyrrolo[3,2-f]benzoxazol-6-one
2-(4-pyridinyl)-7-methyl-5,7-dihydropyrrolo[3,2-f]benzoxazol-6-one
2-(4-pyridinyl)-7-ethyl-5,7-dihydropyrrolo[3,2-f]benzoxazol-6-one
2-(4-pyridinyl)-7-isopropyl-5,7-dihydropyrrolo[3,2-f]benzoxazol-6-one
2-(4-pyridinyl)-7-(2-methylpropyl)-5,7-dihydropyrrolo[3,2-f]benzoxazol-6-one
2-(4-pyridinyl)-7-cyclopentyl-5,7-dihydropyrrolo[3,2-f]benzoxazol-6-one
2-(4-pyridinyl)-7-methyl-7-ethoxycarbonyl-5,7-dihydropyrrolo[3,2-f]benzoxazol-6-one
2-(4-pyridinyl)-7-methyl-7-hydrazinocarbonyl-5,7-dihydropyrrolo[3,2-f]benzoxazol-6-one
2-(4-pyridinyl)-5,7-dihydropyrrolo[3,2-f]benzoxazol-6-one
2'-(4-pyridinyl)-5',7'-dihydrospiro[cyclopentane-1,7'-pyrrolo[3,2-f]benzoxazol]-6'-one
2-(2,3-dimethyl-6-quinoxalinyl)-7,7-dimethyl-5,7-dihydropyrrolo[3,2-f]benzoxazol-6-one
2-(4-[1,8]-naphthyridinyl)-7,7-dimethyl-5,7-dihydropyrrolo[3,2-f]benzoxazol-6-one 2-(4-pyridinyl)-7,7-dipropyl-5,7-dihydropyrrolo[3,2-f]benzoxazol-6-one.

The following Examples are given for the purpose of illustrating the present invention:

EXAMPLE 1

2-(4-Pyridinyl)-7,7-dimethyl-5,7-dihydropyrrolo[3,2-f]benzoxazol-6-one 4 g. 1,3-Dihydro-3,3-dimethyl-6-hydroxy-5-nitro-2H-indol-2-one in 100 ml. glacial acetic acid were hydrogenated in the presence of 1 g. 10% palladium/charcoal at ambient temperature and normal pressure until 1.3 liters of hydrogen had been taken up. The catalyst was filtered off and 2.1 ml. 4-pyridinecarbaldehyde were poured into the filtrate, the solution thereby becoming yellow-orange coloured. While stirring, air was passed through the solution for 3 days, whereafter it was evaporated to dryness in a vacuum, the residue was digested with an aqueous solution of ammonia and water and purified by column chromatography (800 ml. silica gel; elution agent dichloromethane:methanolic ammonia=20:1 v/v). The appropriate fractions were evaporated in a vacuum and the crystalline residue was digested with ethanol and filtered off with suction to give 4.0 g. of beige crystals which were recrystallised from ethanol with treatment with fullers' earth. There were obtained 2.5 g. of the title compound in the form of colourless crystals; m.p. 336°-338° C. Yield 49% of theory.

The starting material was prepared as follows:

1,3-Dihydro-3,3-dimethyl-6-hydroxy-5-nitro-2H-indol-2-one 4.5 g. 1,3-Dihydro-3,3-dimethyl-6-hydroxy-2H-indol-2-one were added portionwise, with vigorous stirring, to 35 ml. 65% nitric acid which was cooled with a mixture of ice and salt. The reaction mixture was further stirred in the cold for 10 minutes, diluted with ice/water to 150 ml. and the crystalline precipitate filtered off with suction and subsequently washed with water to give 4.1 g. (73% of theory) of the title compound in the form of yellow crystals; m.p. 244°-247° C.

EXAMPLE 2

2-(4-Pyridinylmethyl)-7,7-dimethyl-5,7-dihydropyrrolo[3,2-f]benzoxazol-6-one 4.52 g. 5-Amino-1,3-dihydro-3,3-dimethyl-6-hydroxy-2H-indol-2-one hydrochloride and 3.65 g. 4-pyridylacetic acid were heated in 20 g. polyphosphoric acid for 30 minutes to 170° C. and the reaction mixture subsequently poured on to ice. A concentrated aqueous solution of ammonia was added thereto to give a pH of 10, the precipitate obtained was filtered off with suction, successively washed with water, methanol and diethyl ether and then dried to constant weight to give 3.20 g. (55% of theory) of the title compound; m.p. 208°-211° C.

The starting material was prepared as follows:

5-amino-1,3-dihydro-3,3-dimethyl-6-hydroxy-2H-indol-2-one hydrochloride 22.2 g. 1,3-Dihydro-3,3-dimethyl-6-hydroxy-5-nitro-2H-indol-2-one were hydrogenated in 500 ml. methanol in the presence of 5 g. 10% palladium on charcoal. After 2.5 hours, 6.3 liters of hydrogen had been taken up, whereafter the reaction mixture was filtered, the filtrate evaporated to dryness, the residue washed with diethyl ether and then dried to constant weight, the title compound being obtained in a yield of 98% of theory; m.p. >250° C.

EXAMPLE 3

2-(1,2,3-Thiadiazol-4-yl)-7,7-dimethyl-5,7-dihydropyrrolo[3,2-f]benzoxazol-6-one 1.5 g. N-(1,3-dihydro-3,3-dimethyl-6-hydroxy-2(2H)-oxoindol-5-yl)-1,2,3-thiadiazole-4-carboxamide in 10 g. polyphosphoric acid was heated for 10 minutes to 130° C., the reaction mixture was poured on to ice, concentrated aqueous ammonia solution was added thereto to give a pH of 8-9, the precipitate obtained was filtered off with suction, successively washed with water, methanol and diethyl ether and then dried to constant weight to give 1 g. (71% of theory) of the title compound; m.p. >250° C.

The starting material was prepared as follows:

N-(1,3-dihydro-3,3-dimethyl-6-hydroxy-2(2H)-oxoindol-5-yl)-1,2,3-thiadiazole-4-carboxamide 0.8 g. 1,2,3-Thiadiazole-4-carboxylic acid in 7 ml. dichloromethane was added dropwise at 0° C. to 1.4 g. 5-amino-1,3-dihydro-3,3-dimethyl-6-hydroxy-2H-indole-6-one hydrochloride and 1.6 ml. triethylamine in 30 ml. dichloromethane. After stirring for 1 hour at ambient temperature, the precipitate obtained was filtered off with suction, washed with water and dried to constant weight to give 1.5 g. (92% of theory) of the title compound. Mass spectrum: m/e=376 (M+ of the TMS derivative).

EXAMPLE 4

2-(2-Methoxy-6-methyl-3-pyridinyl)-7,7-dimethyl-5,7-dihydropyrrolo[3,2-f]benzoxazol-6-one This was obtained analogously to Example 1 in a yield of 54% of theory after chromatography on silica gel (ethyl acetate/heptane=1:1 v/v) by the reaction with 2-methoxy-5-methylpyridinyl-3-aldehyde instead of 4-pyridinecarbaldehyde; m.p. 236°-238° C.

EXAMPLE 5

2-(2-Thienyl)-7,7-dimethyl-5,7-dihydropyrrolo[3,2-f]benzoxazol-6-one

This was obtained analogously to Example 1 in a yield of 35% of theory after recrystallisation from ethanol by reaction with 2-thiophenaldehyde instead of 4-pyridinecarbaldehyde; m.p. 276°-280° C.

EXAMPLE 6

2-(2-Furyl)-7,7-dimethyl-5,7-dihydropyrrolo[3,2-f]benzoxazol-6-one

This was obtained analogously to Example 1 in a yield of 25% of theory after recrystallisation from ethanol by reaction with furfural instead of 4-pyridinecarbaldehyde; m.p. 240°-245° C.

EXAMPLE 7

2-(2-Imidazo[1,2-a]pyridinylmethyl)-7,7-dimethyl-5,7-dihydropyrrolo[3,2-f]benzoxazol-6-one This was obtained analogously to Example 2 in a yield of 37% of theory by reaction with 2-(2-imidazo[1,2-a]pyridinylacetic acid instead of 4-pyridylacetic acid; m.p. 205°-208° C.

EXAMPLE 8

2-(2-(4-Pyridinyl)-ethenyl)-7,7-dimethyl-5,7-dihydropyrrolo[3,2-f]benzoxazol-6-one This was obtained analogously to Example 2 in a yield of 60% of theory by reaction with 3-(4-pyridyl)acrylic acid instead of 4-pyridylacetic acid; m.p. >250° C.

EXAMPLE 9

2-(2-(4-Pyridinyl)-ethyl)-7,7-dimethyl-5,7-dihydropyrrolo[3,2-f]benzoxazol-6-one This was obtained analogously to Example 2 in a yield of 54% of theory by reaction with 3-(4-pyridinyl)-propionic acid instead of 4-pyridylacetic acid; m.p. 192°-195° C.

EXAMPLE 10

2-(2-Methyloxazol-4-yl)-7,7-dimethyl-5,7-dihydropyrrolo[3,2-f]benzoaxazol-6-one

This was obtained analogously to Example 2 in a yield of 3% of theory by reaction with 2-methyloxazole-4-carboxylic acid instead of 4-pyridylacetic acid; m.p. >250° C.

EXAMPLE 11

2-(4-Pyridazinyl)-7,7-dimethyl-5,7-dihydropyrrolo[3,2-f]benzoxazol-6-one

This was obtained analogously to Example 2 in a yield of 39% of theory by reaction with 4-pyridazinecarboxylic acid instead of 4-pyridylacetic acid; m.p. >250° C.

EXAMPLE 12

2-(2-Pyrazinyl)-7,7-dimethyl-5,7-dihydropyrrolo[3,2-f]benzoxazol-6-one

This was obtained analogously to Example 2 in a yield of 48% of theory by reaction with 2-pyrazinecarboxylic acid instead of 4-pyridylacetic acid; m.p. >250° C.

EXAMPLE 13

2-(3-Pyridinyl)-7,7-dimethyl-5,7-dihydropyrrolo[3,2-f]benzoxazol-6-one

This was obtained analogously to Example 1 in a yield of 10% of theory after recrystallisation from ethanol by reaction with 3-pyridinealdehyde instead of 4-pyridine carbaldehyde; m.p. 285°-287° C.

EXAMPLE 14

2-(2-Pyridinyl)-7,7-dimethyl-5,7-dihydropyrrolo[3,2-f]benzoaxazol-6-one

This was obtained analogously to Example 1 in a yield of 10% of theory after recrystallisation from ethanol by reaction with 2-pyridinealdehyde instead of 4-pyridinealdehyde; m.p. 272°-275° C.

EXAMPLE 15

2-(4-Quinolinyl)-7,7-dimethyl-5,7-dihydropyrrolo[3,2-f]benzoxazol-6-one

This was obtained analogously to Example 1 in a yield of 13% of theory after recrystallisation from ethanol by reaction with 4-quinolinealdehyde instead of 4-pyridinecarbaldehyde; m.p. >300° C.

EXAMPLE 16

2-(N-Oxypyridinyl)-7,7-dimethyl-5,7-dihydropyrrolo[3,2-f]benzoxazol-6-one 12 ml. 30% Hydrogen peroxide were added dropwise to 4.0 g. 2-(4-pyridinyl)-7,7-dimethyl-5,7-dihydropyrrolo[3,2-f]benzoxazol-6-one in 80 ml. glacial acetic acid. The reaction mixture was stirred for 1 week at ambient temperature, water was then added thereto and the pH value was adjusted to 6 by the addition of a concentrated aqueous solution of ammonia. The precipitated product was filtered off with suction and purified by column chromatography (silica gel 60, dichloromethane/methanol=20:1 v/v). The pure fractions were evaporated and the residue was recrystallised from ethanol/water to give 1.4 g. of the title compound in the form of pale yellow crystals; m.p. 340°-341° C.

TEST PROTOCOL

Immunopharmacological effects of new heterocyclically substituted 5,7-dihydro-pyrrolo-[3,2-f]benzoxazole-6-ones.

I. Selective retardation of lymphocyte proliferation in vitro.

Method:

Mice splenocytes are adjusted in a RPMI 1640-medium (with the conventional additives of streptomycin, penicillin, L-glutamine and 10% FKS) to a cell density of $2 \times 10^6$ living cells/ml. 220 microliters of this cell suspension are added to 20 microliters of an 11 fold concentrated solution of the substance dilution to be tested. 0.5 micrograms of concanavaline A in 10 microliters PBS are added to each culture as the mitogenic stimulus. 20 microliters of a 3H-thymidine solution are added to each culture 5 hours before the end of the 24-hour incubation period and the proliferation of the cells are determined by means of the inserted radioactivity.

Each week a meth A-cell line will be temporarily implanted in the mice as ascites. After puncturing the ascites the cells are washed and adjusted with a.m. medium to a cell density of $5 \times 10^4$ viable cells/ml. 200 microliters of this suspension are pipetted into the of a microtiter plate and the diluted substances which have to be tested are added as mentioned above.

3 hours before the end of the 24-hour incubation period 3H-thymidine is added at intervals. The presence of radioactive thymidine is determined by the proliferation of the individual cultures.

Table 1 demonstrates that the retardation of the proliferation of mitogenic-stimulated lymphocytes has a much stronger effect than the autokrin/parakrin growing meth A-cells of the mouse.

II. Retardation of the Host-versus-Graft (HvG)-reaction in the popliteal lymphe node assay in the mouse.

Method:

$5 \times 10^6$ splenocytes of mice of the strain (Balb/c × C57B1/6) F1 in 0,05 ml PBS are administered by subplantar injection in the hind paw of mice of the strain Balb/c. The same number of splenocytes of Balb/c mice are injected into the other hind paw. The animals are treated intraperitoneally once a day with the substances to be tested in a 0.5% tylose suspension, starting on day 0, 2 hours before the injection of the cells, until day 3. On day 4 after the cell injection, the animals are sacrificed, and the weights of the popliteal lymph nodes are determined. The differences between syngenic and semiallogenic reaction are calculated, and the retardation of the HvG reaction is determined by comparison to an untreated control group.

Table 2 summarizes the results concerning the retardation of the HvG-reaction of a few representatives of the claimed oxindoles at dosages of 20 mg/kg body weight per day. Especially the compound of example 1 causes highly significant retardation of the development of HvG-reaction at the tested dose (double-sided t-Test for spot-tests of the same scope).

According to the methods described above, the non-specific retardation of lymphocyte proliferation is recorded. This retardation of lymphocytes is a model for the proliferation of immuno-competent cells. The results show that these cells are influenced in a more sensitive way by the compounds of the present invention than by MethA-fibrosarkoma cells. This means that the inventive compounds have a selective immunopharmacological cal retardation effect.

It will be understood that the specification and examples are illustrative but not limitative of the present invention and that other embodiments within the spirit and scope of the invention will suggest themselves to those skilled in the art.

TABLE 1

| | | Selective retardation of lymphocyte proliferation in vitro. | | | | | | | | |
|---|---|---|---|---|---|---|---|---|---|---|
| | | % retardation | | | | | | | | |
| | | Lymphocyte Proliferation (mg/l) | | | | | Meth A-tumor cell Proliferation (mg/l) | | | |
| Compound | test | 10 | 3 | 1 | 0,3 | 0,1 | 10 | 3 | 1 | 0,3 | 0,1 |
| Example 1 | 1 | 97 | 53 | 29 | 29 | 19 | −86 | −77 | −35 | −13 | −19 |
| | 2 | 92 | 15 | −9 | −2 | −15 | 32 | 24 | 22 | 5 | 43 |
| | 3 | 93 | 20 | −1 | −60 | −72 | −22 | −47 | −9 | −7 | −25 |
| | 4 | 98 | 73 | 39 | 23 | 14 | 22 | −68 | −32 | −12 | −25 |

TABLE 2

| | | Retardation of Host-versus-Graft (HvG)-reaction in popliteal lymph node assay in the mouse. | | |
|---|---|---|---|---|
| | | Lymph node weight (mg) | | |
| comp. | dose (mg/kg × d) | Syngenic Reaction (n = 7) x ± SD | Semiallogene Reaction (n = 7) x ± SD | % retard. referring to control |
| Ex. 1 | 0 | 1,18 + 0,35 | 5,52 + 0,94 | — |
| | 20 | 0,91 + 0,20 | 1,86 + 0,54 | 78 (p < 0,001) |
| Ex. 5 | 0 | 1,20 + 0.26 | 5,36 + 0,52 | — |
| | 20 | 1,10 + 0,33 | 4,34 + 0,62 | 22 (p < 0,05) |
| Ex. 2 | 0 | 1,31 + 0,18 | 6,44 + 0,69 | — |
| | 20 | 1,17 + 0,21 | 5,27 + 0,83 | 20 (p < 0,05) |

We claim:

1. A compound of the formula:

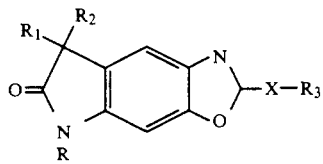

(I)

wherein

R is hydrogen or a $C_1$–$C_6$ alkyl, $R_1$ is hydrogen or a $C_1$–$C_6$ alkyl, $C_2$–$C_6$-alkenyl or a $C_3$–$C_8$-cycloalkyl radical, $R_2$ is hydrogen or a $C_1$–$C_6$ alkyl, $C_2$–$C_6$-alkenyl, $C_1$–$C_6$-alkylcarbonyl, $C_1$–$C_6$-alkoxycarbonyl, aminocarbonyl or hydrazinocarbonyl radical or $R_1$ and $R_2$, together with the carbon atom to which they are attached, form a $C_3$–$C_8$ cycloalkyl ring, X is a valency bond or $C_1$–$C_8$ alkylene or vinylene, $R_3$ is pyridinyl unsubstituted or substituted one or more times by alkyl, alkoxy, alkoxycarbonyl, carboxyl, alkylthio, hydroxyl, nitro, amino, halogen; and the tautomer, optically-active form and physiologically acceptable salt thereof with inorganic and organic acids.

2. A compound of the formula I of claim 1, wherein R is hydrogen, $R_1$ is hydrogen or a $C_1$–$C_4$-alkyl, $R_2$ is hydrogen or a $C_1$–$C_4$-alkyl or $R_1$ and $R_2$, together with the carbon atom to which they are attached, form a $C_5$–$C_6$-spirocycloalkyl ring, and X is a valency bond or a $C_1$–$C_4$-alkylene or vinylene.

3. A compound of claim 2 wherein $R_1$ and $R_2$ are the same and are $C_1$–$C_4$-alkyl.

4. A compound of claim 1 wherein $R_1$ is hydrogen, methyl, ethyl or allyl and $R_2$ is hydrogen, methyl, ethyl, acetyl, propionyl, methoxycarbonyl, ethoxycarbonyl or hydrazinocarbonyl.

5. A compound of claim 1 wherein $R_1$ and $R_2$ are methyl.

6. A compound of claim 1 wherein $R_1$ is methyl, ethyl, isopropyl, isobutyl, pentyl, cyclopentyl, cyclohexyl or allyl and $R_2$ is acetyl, propionyl methoxycarbonyl, ethoxycarbonyl and hydrazinocarbonyl.

7. A compound of claim 1 wherein $R_1$ and $R_2$ form a spirocyclopropyl, spirocyclobutyl, spirocyclopentyl or spirocyclohexyl ring.

8. A compound of claim 1 wherein R is hydrogen, methyl, ethyl or isopropyl.

9. A compound of claim 1 wherein X is methylene, ethylene, propylene or butylene.

10. A compound of claim 1 wherein R is hydrogen, $R_1$ and $R_2$ are methyl or $R_1$ and $R_2$, together with the carbon atom to which they are attached, form a spirocyclopentyl ring, and X is a valency bond, a $C_1$–$C_4$-alkylene or vinylene.

11. The compound designated 2-(4-Pyridinyl-7,7-dimethyl-5,7-dihydropyrrolo-[3,2-f]benzoxazol-6-one or a pharmacologically acceptable salt thereof.

12. The compound designated 2-(4-Pyridinylmethyl)-7,7-dimethyl-5,7-dihydropyrrolo-[3,2-f]benzoxazol-6-one or a pharmacologically acceptable salt thereof.

13. A pharmaceutical composition for the treatment of autoimmune disease disorders, and graft rejection reaction comprising a pharmaceutically effective amount of at least one of the compound of claim 1 in a pharmaceutically acceptable carrier.

14. A pharmaceutical composition for the treatment of and suppression of autoimmune disease, and graft rejection reactions comprising administering a pharmaceutically effective amount of at least one of the compounds of claims 11, or 12 in a pharmaceutically acceptable carrier.

15. A method for the treatment of and suppression of autoimmune disease, and graft rejection reactions in a mammalian host comprising administering an effective amount of at least one of a compound of claim 1 in a pharmaceutically acceptable carrier.

16. A method for the treatment of and suppression of autoimmune disease, and graft rejection reactions in a mammalian host comprising administering an effective amount of at least one of a compound of claim 11, or 12.

17. A method for the treatment of diseases in a mammalian host in which polyclonal B cell activation or proliferation is a factor which comprises administering an effective amount of a compound of claims 1 or 2.

* * * * *

UNITED STATES PATENT AND TRADEMARK OFFICE
CERTIFICATE OF CORRECTION

PATENT NO. : 5,057,526
DATED : October 15, 1991
INVENTOR(S) : von der Saal et al.

It is certified that error appears in the above-identified patent and that said Letters Patent is hereby corrected as shown below:

Col. 17, line 55:   change "benzoaxazol" to -- benzoxazol --.

Col. 18, line 44:   after "pipetted into the" insert -- wells --.

Col. 19, line 19:   delete "cal".

Signed and Sealed this

Fifth Day of October, 1993

Attest:

Attesting Officer

BRUCE LEHMAN

Commissioner of Patents and Trademarks